US010905638B2

(12) United States Patent
Hilke et al.

(10) Patent No.: US 10,905,638 B2
(45) Date of Patent: Feb. 2, 2021

(54) DENTIFRICE COMPOSITION

(71) Applicant: Biodental Remin Ltd, Macksville (AU)

(72) Inventors: Bjorn Kentaro Hilke, Auckland (NZ); Alexander Ian McIntosh, North Turramurra (AU); Rosi Hilke, Auckland (NZ)

(73) Assignee: BIODENTAL REMIN LTD., New South Wales (AU)

( * ) Notice: Subject to any disclaimer, the term of this patent is extended or adjusted under 35 U.S.C. 154(b) by 0 days.

(21) Appl. No.: 15/128,753

(22) PCT Filed: Mar. 25, 2015

(86) PCT No.: PCT/AU2015/050133
§ 371 (c)(1),
(2) Date: Sep. 23, 2016

(87) PCT Pub. No.: WO2015/143507
PCT Pub. Date: Oct. 1, 2015

(65) Prior Publication Data
US 2018/0214356 A1    Aug. 2, 2018

(30) Foreign Application Priority Data
Mar. 25, 2014 (AU) ................................ 2014901059

(51) Int. Cl.
| | | |
|---|---|---|
| *A61K 8/19* | (2006.01) | |
| *A61Q 11/00* | (2006.01) | |
| *A61K 8/21* | (2006.01) | |
| *A61K 8/11* | (2006.01) | |
| *A61K 8/73* | (2006.01) | |
| *A61K 8/92* | (2006.01) | |
| *A61K 8/24* | (2006.01) | |

(52) U.S. Cl.
CPC ............. *A61K 8/19* (2013.01); *A61K 8/11* (2013.01); *A61K 8/21* (2013.01); *A61K 8/24* (2013.01); *A61K 8/731* (2013.01); *A61K 8/927* (2013.01); *A61Q 11/00* (2013.01); *A61K 2800/56* (2013.01); *A61K 2800/624* (2013.01); *A61K 2800/651* (2013.01)

(58) Field of Classification Search
CPC .......... A61Q 11/00; A61K 8/731; A61K 8/21; A61K 8/11; A61K 8/927; A61K 8/24; A61K 8/19; A61K 2800/56; A61K 2800/651; A61K 2800/624
See application file for complete search history.

(56) References Cited

U.S. PATENT DOCUMENTS

| | | | | |
|---|---|---|---|---|
| 3,471,613 A | * | 10/1969 | Gagolski | A61K 8/55 424/57 |
| 4,203,966 A | | 5/1980 | Faunce et al. | |
| 4,292,306 A | | 9/1981 | Faunce et al. | |
| 4,923,683 A | | 5/1990 | Sakuma et al. | |
| 5,908,879 A | | 6/1999 | Kawashima et al. | |
| 5,976,507 A | * | 11/1999 | Wong | A61K 8/11 424/451 |
| 2006/0171904 A1 | | 8/2006 | Vogel et al. | |
| 2006/0177383 A1 | * | 8/2006 | Gebreselassie | A23G 4/064 424/49 |
| 2010/0047191 A1 | * | 2/2010 | Fowler | A61K 8/19 424/52 |

FOREIGN PATENT DOCUMENTS

| | | |
|---|---|---|
| JP | 646213 A1 | 1/1989 |
| JP | 2004196698 A | 7/2004 |
| JP | 2006501268 A | 1/2006 |
| JP | WO2010061932 A1 | 4/2012 |
| JP | 2013529633 A | 7/2013 |
| WO | 1999/062471 A1 | 12/1999 |

(Continued)

OTHER PUBLICATIONS

Dawes, C., What is the critical pH and Why Does a Tooth Dissolve in Acid?, Journal of hte Canadian Dental Association, 2003, vol. 69, No. 11, pp. 722-724.

(Continued)

*Primary Examiner* — Lezah Roberts
(74) *Attorney, Agent, or Firm* — Charles C. Achkar; Ostrolenk Faber LLP.

(57) ABSTRACT

A dentifrice composition comprises a toothpaste carrier having a pH of about 7 to about 10 and a calcium ion source and a fluoride ion source wherein the calcium ion source is unencapsulated and the fluoride ion source is encapsulated or coated in a coating impermeable to the toothpaste carrier. The coating degrades to release fluoride ions when mechanically agitated by a toothbrush in an oral cavity surface. In a second embodiment, the dentifrice composition comprises an aqueous toothpaste carrier having a pH of about 7 to about 10 with an unencapsulated calcium ion source and a fluoride ion source having a pH of between 3 to less than 7 wherein the fluoride ion source is encapsulated in a first (or inner) impermeable coating adapted to degrade to release the fluoride ions in the presence of a toothpaste carrier. The first coating is encased in a second (or outer) impermeable coating adapted to resist degradation in the presence of the toothpaste carrier and to mechanically degrade to expose the first (or inner coating) which degrades to release the fluoride ions in response to application of the dentifrice composition to an oral cavity surface.

18 Claims, No Drawings

(56) References Cited

FOREIGN PATENT DOCUMENTS

WO     2010/129309 A2    11/2010
WO     2014/043385 A2     3/2014

OTHER PUBLICATIONS

PCT International Search Report issued in PCT/AU2015/050133 dated Apr. 29, 2015.
Written Opinion of the International Searching Authority issued in PCT/AU2015/050133 dated Apr. 29, 2015.
International Preliminary Report on Patentability issued in PCT/AU2015/050133 dated Sep. 27, 2016.
Japanese Office Action issued in counterpart application 2017-501434, dated Apr. 2, 2019.

* cited by examiner

DENTIFRICE COMPOSITION

CROSS REFERENCE TO RELATED APPLICATIONS

The present application is a § 371 National Phase application based on PCT/AU2015/050133 filed Mar. 25, 2015, which claims the benefit of Australian patent application No. 2014901059, filed Mar. 25, 2014 the subject matter of each of which is incorporated by reference in their entirety.

FIELD OF THE INVENTION

The present invention relates to dentifrice compositions and, in particular, to a dentifrice composition including at least two reactive ingredients.

BACKGROUND ART

The invention has been developed primarily for use as a toothpaste or dentifrice and will be described hereinafter with reference to this application. However, it will be appreciated that the invention is not limited to this particular field of use and is applicable to other topical compositions to be applied to the oral cavity to improve oral hygiene, clean teeth or remineralise teeth, for example.

For many decades, it has been well known for toothpaste to include fluoride salts such as sodium fluoride or stannous fluoride as protective or anticaries agents. These fluoride sources, most often a sodium monofluorophosphate salt, are disposed in a toothpaste carrier substance.

The toothpaste carrier substance typically has a pH greater than 7 to about 8.5 and includes other ingredients such as abrasives and mouth feel agents. Once applied to teeth the fluoride ions are caused to react and bond as fluoride ions into a crystal lattice forming the enamel of the teeth. The fluoride ions bond with hydroxyapatite to produce a more acid resistant tooth enamel and repair lattice irregularities on the tooth enamel surface which is predominantly composed of the hydroxyapatite.

It has long been known to attempt to maximise the remineralisation or repair potential of toothpastes. One of the means by which this is achieved is by placing two complementary but otherwise reactive components in the toothpaste.

WO99/62471 (Wong and Prencipe) discloses an aqueous dentifrice composition having a calcium salt such as calcium acetate or calcium chloride that is coated in a water impermeable shell and which is disposed in a toothpaste carrier containing an aqueous fluoride salt such as sodium monofluorophosphate. The shell of the calcium salt is formed from an ethyl cellulose polymer plasticised by means of triethylcitrate.

In use, the toothpaste carrier is placed on a toothbrush which is then brushed on teeth or other areas of the oral cavity. This process mechanically ruptures the calcium salt coating thereby releasing and allowing a reaction with the fluoride.

This is believed to improve the efficacy of aqueous fluoride salts on teeth by first allowing exposure to the fluoride ion and then releasing the calcium ion source. U.S. Pat. No. 5,045,305 relates to a means of depositing fluoride ions on the teeth via a semi-permeable coating. Wong et al claimed to have improved on this by exposing teeth to a source of fluoride ions then releasing calcium ions from a coated calcium ion source. However, there do not appear to be any proven results indicating tooth remineralisation at a rate that can be of practical benefit.

GENESIS OF THE INVENTION

The genesis of the invention is a desire to provide a fluoride ion source together with a phosphate ion source and/or a calcium ion source to form a dentifrice composition in which the fluoride, phosphate and/or calcium sources are stable until used, or to provide a useful alternative.

SUMMARY OF THE INVENTION

According to a first aspect of the invention there is provided a dentifrice composition comprising a toothpaste carrier having a pH of about 7 to about 10, the dentifrice composition including a calcium ion source and a fluoride ion source wherein the calcium ion source is un-encapsulated and the fluoride ion source is encapsulated or coated in a coating impermeable to the toothpaste carrier whereby the coating degrades to release fluoride ions when mechanically agitated by a toothbrush in an oral cavity surface.

It can therefore be seen that there is advantageously provided a dentifrice composition that has a carrier material with a calcium ion source that is able to be applied to the oral cavity and tooth surfaces before the fluoride ion source is made available. The fluoride ion source has a coating or encapsulation that is adapted to degrade upon application with a toothbrush where the coating material is adapted to be compromised to release or expose the fluoride ion source. Advantageously also, either a suitably adapted enteric coating or other rupturable impermeable coating can be used so the brushing action releases the fluoride ions.

Furthermore, in preferred embodiments, the toothpaste carrier material is a calcium sucrose phosphate complex known as Anticay® which is the registered trademark of Biodental Remin Ltd, Sydney, Australia, providing a source of both calcium ions and phosphate ions which also includes a coated fluoride ion source. The oral cavity and tooth surfaces are first exposed to the calcium ion source and then by mechanical action releasing the fluoride ion which appears to the inventors to provide significant remineralisation potential.

According to a second aspect of the invention there is provided a dentifrice composition comprising an aqueous toothpaste carrier having a pH of about 7 to about 10, the dentifrice composition including an unencapsulated calcium ion source and a fluoride ion source having a pH of between 3 to less than 7 wherein the fluoride ion source is encapsulated in a first (or inner) impermeable coating adapted to degrade to release the fluoride ions in the presence of a toothpaste carrier and wherein the first coating is encased in a second (or outer) impermeable coating adapted to resist degradation in the presence of the toothpaste carrier and to mechanically degrade to expose the first (or inner coating) which degrades to release the fluoride ions in response to application of the dentifrice composition to an oral cavity surface.

It can therefore be seen that there is advantageously provided a dentifrice composition that has an aqueous carrier material with calcium sucrose phosphate complex providing a source of both calcium ions and phosphate ions which also includes a coated fluoride ion source. The oral cavity and tooth surfaces are first exposed to the calcium ion and phosphate ion source and then by mechanical action releasing the fluoride ion which appears to provide significant remineralisation potential.

DETAILED DESCRIPTION

Preferred embodiments of the invention will now be described by way of the following non limiting examples.

It is known to have calcium and phosphate ion sources available in modern remineralising toothpaste ingredients. For example, as used in Novamin™ (Glaxosmith Kline) or as used in Recaldent™ (Cadbury Enterprises Pte. Ltd). However, any other calcium ion source, and preferably with an available phosphate ion source, can include any preferred known materials including calcium fluoride, calcium maleate, calcium tartrate, inter alia.

A potentially significantly more promising material in its tooth remineralisation and tooth repair efficacy is calcium sucrose phosphate complex, Anticay®. The preferred embodiments are hereinafter described with reference to calcium sucrose phosphate complex, however as noted any calcium ion source can be used. The calcium sucrose complex provides a highly water soluble source of calcium ions and also provides a source of phosphate ions. Phosphate ions are known to be integral to the structure of hydroxyapatite.

Calcium sucrose phosphate complex is a well-known remineralisation and anti-caries material that can be used in dentifrices. Reference is made to U.S. Pat. No. 3,375,168 (Curtin et al) discloses the manufacture and isolation of calcium sucrose phosphate complexes and that disclosure is incorporated herein in its entirety by cross reference.

In the preferred embodiment one or more species of calcium sucrose phosphate complexes as in Curtain et al are provided as particles of a size between 10 μm and 100 μm. These were combined with a toothpaste carrier. By weight of toothpaste carrier, approximately 1-5% calcium sucrose phosphate complex is added but preferably any amount between 0.5% to 70% of calcium sucrose phosphate complexes can be added. Most preferably, the calcium sucrose phosphate complexes are provided to allow an available concentration of calcium ions in the oral cavity in the amount of 500 ppm to 50,000 ppm. Also advantageously, the phosphate in the calcium sucrose phosphate complexes assist in buffering the toothpaste carrier.

It will be appreciated, however, that any preferred calcium ion source can be used as desired whether it be aqueous or non-aqueous. For example, the calcium ion source may include any one or a combination of calcium carbohydrate phosphate complex; calcium acetate; calcium chloride; calcium citrate; calcium fluoride; calcium maleate; and calcium tartrate. Of course, other known calcium ion and phosphate ion sources can be added to the toothpaste carrier material, such as Recaldent™ (calcium phosphopeptide-amorphous calcium phosphate) or Novamin™ (calcium sodium phosphosilicate) provided by Cadbury Enterprises Pte Ltd and GlaxoSmithKline respectively.

The toothpaste carrier of the preferred embodiment was formed from:
One or more calcium sucrose phosphate complexes preferably in the amount 5% w/w;
Calcium phosphate most preferably having particle sizes of the order of 1 microns to 50 microns and 10 nm to 500 nm, in the amount 39.7% w/w;
Glycerine 20% w/w;
Sorbitol 2.07% w/w;
Sodium laurel sulphate 2.8% w/w;
Saccharin 0.1% w/w;
Sodium Benzoate 0.1% w/w;
Flavour 0.9%;
Sodium monofluorophosphate particles coated in an ethyl cellulose polymer plasticised by means of triethylcitrate such that the sodium fluoride is present in the amount of $2 \times 10^{-6}$% to 2.0% w/w to provide an available fluoride ion source of between 0.0025 ppm to approximately 9000 ppm; and
Purified water to 100%.

In another example, the toothpaste carrier can be formed from: water; an abrasive in the form of hydroxyapatite or zeolite; sodium lauryl sulphate surfactant; a sugar alcohol in the form of sorbitol; and one or more calcium sucrose phosphate complexes preferably in the amount of 10% w/w;

It will be appreciated that any preferred toothpaste carrier composition can be used. Preferably this is water based and can include simply calcium sucrose phosphate complexes mixed with water. Similarly, the toothpaste carrier need not be in the form of a conventional paste but can also include a gel.

To the toothpaste carrier of the preferred embodiment having the calcium sucrose phosphate complexes was added between $2 \times 10^{-6}$% to 2.0% sodium fluoride. This is in the form of particles less than 100 μm and most preferably less than 20 μm in size. Ideally, the fluoride ion source is added in an amount to provide available fluoride ions in the amount of 0.0025 ppm to 9000 ppm. The sodium fluoride particles were encased in a water insoluble and non-permeable coating in the form of an ethyl cellulose polymer plasticised by means of triethylcitrate or other coating which is capable of encasing the fluoride ion source in the aqueous environment.

It will be appreciated that any preferred fluoride ion source can be used such as any one or more from sodium fluoride, sodium monofluorophosphate; potassium fluoride; calcium fluoride; magnesium fluoride; stannous fluoride; stannous monofluorophosphate; copper fluoride or any other fluoride ion source. In the case of fluoride ion sources having a pH around neutral or greater such as sodium monofluorophosphate which is commonly used in dentifrice compositions, these particles can be encased in ethyl cellulose as above or any other preferred coating materials that are used for microencapsulation for various situations adapted to provide an impermeable barrier to the fluoride ion source in the toothpaste carrier where the fluoride ion source is able to be ruptured during brushing with a toothbrush. For example, the coating material can one or a combination of two or more of shellac, a wax, a fatty acid, a methyl cellulose, a fluoropolymer, a poly-vinyl alcohol-polyethylene glycol (PVA-PEGs), a polyurethane, an acrylic, an alkyd; a polyester, hydroxyl propyl methyl cellulose (HPMC) or HPMC acetate succinate; polyvinyl acetate phthalate (PVAP); and polyvinyl-pyrrolidine (PVP).

The fluoride ion coating needs to keep the fluoride ion source encapsulated in the presence of the toothpaste carrier material of a pH between 7 and 10 so that brushing breaks the coating. Some materials known to be used as enteric coatings can be employed once adapted to resist degradation in the toothpaste carrier environment, however, these typically resist degradation in pH ranges below about 5 and acrylics for example as above can be used for pH environments between 7 and 10.

Once the dentifrice composition is applied to the oral cavity the calcium sucrose phosphate complexes are exposed to the tooth enamel surfaces. Brushing in the manner such as with a conventional toothbrush or other agitator causes the calcium and phosphate ion rich carrier to contact the teeth thereby improving conditions for allowing the calcium and phosphate ions to bond to the tooth structure. The process of brushing or agitation also causes the fluoride ion source coating to break, dissolve or degrade to expose the fluoride ion source. In this way the fluoride ion source is exposed to the teeth in the oral cavity once the calcium ion and phosphate ion source has already been made available. In the preferred embodiment of a calcium sucrose phosphate complex, phosphate ions are also advantageously released where the toothpaste carrier material includes a phosphate ion availability of the order of 500 ppm to 50,000 ppm.

In the dentifrice composition of the preferred embodiments, it is also possible to regulate the pH and the amounts of available phosphate, calcium and fluoride ions therein, any or all of these ions can be adjusted in concentration or availability to provide for the precipitation of calcium fluoride or formation of fluorapatite in varying amounts if desired. In one particularly preferred embodiment, the pH of the resultant mixture of the toothpaste carrier (including all ingredients) is modified by the inclusion of at least one acid or acidic buffer encapsulated in a water insoluble and impermeable coating adapted to degrade upon application of the toothpaste carrier to the tooth surface.

Upon application, the acid or acidic buffer is released thereby reducing the pH to a predetermined level, preferably between 2.5 and 7. In some embodiments, the pH is between 4 and 6 and in other preferred embodiments it is about 5.5. It will be appreciated that, for example, when mono-di- or tri-calcium phosphates are used the pH will affect the solubility of the calcium such that it increases when the pH is made more acidic so as to free up or make the calcium more available.

In alternative preferred embodiments, the pH of the resultant mixture of the toothpaste carrier (including all ingredients) is modified by the inclusion of at least one alkaline material or buffer encapsulated in a water insoluble and impermeable coating adapted to degrade when in an acidic environment or by application of the toothpaste carrier to the tooth surface by a toothbrush to release the alkaline material and thereby increase the pH to a predetermined level, preferably about a neutral pH. The coating concentrations or thicknesses are such that the time of release of the alkaline material should allow the final pH to be achieved before 2 minutes of brushing time has elapsed. In one preferred embodiment the predetermined final pH is between 6.0 and 8 and more preferably between 6.5 and 7.5 and more preferably 7.5.

It will be appreciated that the preferred embodiments of the dentifrice composition can include where the toothpaste carrier is non-aqueous. The composition may also include one or more antimicrobial materials such as chlorhexidine, Cetylpyridinium chloride (CPC), benzalkonium chloride (BAC), Kappazinc, Kappacin, and stabilised chlorine dioxide. However, any preferred antimicrobial can be used.

It is believed that by coating of the fluoride ion source so as to allow teeth in the oral cavity to be exposed to the calcium and phosphate ion sources and then releasing the fluoride ions, improved tooth enamel remineralisation occurs.

Another preferred embodiment includes a second coating to prevent degradation of the fluoride in being in the form of amine fluoride (also known to be branded as Olaflur™).

The toothpaste carrier of this preferred embodiment was formed from:
One or more calcium sucrose phosphate complexes preferably in the amount 5% w/w;
Hydroxyapatite most preferably having particle sizes of the order of 1 microns to 50 microns and 10 nm to 500 nm, in the amount 39.7% w/w;
Glycerine 20% w/w;
Sorbitol 2.07% w/w;
Sodium laurel sulphate 2.8% w/w;
Saccharin 0.1% w/w;
Sodium Benzoate 0.1% w/w;
Flavour 0.9%;
Amine fluoride (or oluflur being N,N,N'-tris(2-hydroxyethyl)-N'-octadecylpropane-1,3-diamine dihydrofluoride) to provide an available fluoride ion source of between 0.0025 ppm to approximately 9000 ppm; and
Purified water to 100%

The toothpaste carrier can also be formed, for example, from water and an abrasive in the form of hydroxyapatite or zeolite. Sodium lauryl sulphate surfactant and a sugar alcohol in the form of sorbitol is also included. It will be appreciated that any preferred toothpaste carrier composition can be used in this is preferably water based and can include simply calcium sucrose phosphate complexes mixed with water.

In the toothpaste carrier containing the calcium sucrose phosphate complexes between 0.1% to 1.5% amine fluoride (or oluflur being N,N,N-tris(2-hydroxyethyl)-N'-octadecylpropane-1,3-diamine dihydrofluoride) can preferably be added. This is in the form of particles less than 100 and most preferably less than 20 µm in size. Ideally, the fluoride ion source is added in an amount to provide available fluoride irons in the amount of 0.0025 ppm to 9000 ppm.

The fluoride ion source is encapsulated in two coating materials. The first (or inner) amine fluoride coating is composed of HPMC in the most preferred embodiment. This is then coated with a second (or outer) water insoluble coating being shellac in the preferred embodiment. Other polymeric or synthetic water insoluble coating materials can be used as desired. The amine fluoride particles can be encased in a water insoluble and non-permeable coating in the form of hypromellose (HPMC) or PVAP or other coating which is capable of encasing the amine fluoride ion source which typically has a pH of the order of about 4.

Once the amine fluoride is coated with first and second coatings, it is added to the aqueous toothpaste carrier containing the calcium sucrose phosphate complex. The fluoride ion source is then protected from reacting with the calcium sucrose phosphate complexes.

The dentifrice composition is then applied by a brush most preferably to surfaces in the oral cavity, particularly the teeth. The brushing action causes the insoluble second (or outer) coating on the amine fluoride to rupture so as to degrade and expose the first coating. At this stage, the calcium sucrose phosphate complex has been applied to the oral cavity surfaces and this being an aqueous environment degrades or otherwise dissolves the first coating so as to release the amine fluoride. The amine fluoride is then able to bond to the tooth structure and/or freshly deposited calcium and phosphate ions or it may also react with the calcium sucrose phosphate to provide calcium fluoride ions to bond with the tooth enamel. In that way, the calcium ion source is exposed to the teeth first and then the fluoride ions are released.

This preferred embodiment of the dentifrice composition advantageously allows an acidic non-aqueous amine fluoride to be placed in a toothpaste that is of an alkaline pH and no reaction occurs until mechanically applied to an oral cavity surface such as tooth. This is foreseen as advantageous as the double coating of the amine fluoride protects it from the toothpaste carrier material and allows release of the fluoride ions after application, in mechanically breaking the outer coating and allowing degradation of the inner coating.

It will be appreciated that in other preferred embodiments, the amine fluoride can be substituted with a mixture of amine fluoride and stannous fluoride.

Further, it will be appreciated that the amine fluoride can itself be replaced in preferred embodiments with 9-Octadeceylamine hydrofluoride (also known as Dectaflur).

A dentifrice composition of a particularly preferred and advantageous embodiment includes a non-aqueous fluoride ion source having an acidic pH that is disposed within an aqueous carrier material having a calcium carbohydrate phosphate complex and a pH of 6.5-6.7 (calcium carbohydrate phosphate complexes degrade at pH<6.5 over about a 12 month period). A pH of 6.6 is preferred. The aqueous carrier has encapsulated alkaline pH modifiers such as calcium hydroxide which when ruptured or otherwise degraded, release the pH modifiers and cause an elevation in the pH of the mixed product.

In use, the second (outer) coating of the fluoride ion source is mechanically broken and is not water soluble which then exposes the first coating which degrades, dissolves or otherwise erodes to release the fluoride ions once the calcium is freely available and brushing or other application of the toothpaste in the oral cavity has commenced. This releases the acidic fluoride ion source which results in a decrease in the pH of the toothpaste saliva mixture in the mouth to >=5.5. Additional acidic buffers may be incorporated into the fluoride ion source or other acidic pH modifiers, capsules containing an acidic material, may be incorporated to provide the required pH shift.

The encapsulated alkaline pH modifiers are designed to break down after a certain amount of time of exposure to the acidic pH in the oral cavity but they may also be ruptured by the brushing action as they soften. The alkaline pH modifiers are designed to have the effect of raising the pH so that at the end of some brushing period the pH of the material and oral cavity is >7.0.

The foregoing describes only one embodiment of the present invention and modifications, obvious to those skilled in the art, can be made thereto without departing from the scope of the present invention.

The term "comprising" (and its grammatical variations) as used herein is used in the inclusive sense of "including" or "having" and not in the exclusive sense of "consisting only of".

The invention claimed is:

1. A dentifrice composition comprising a toothpaste carrier having a pH of 7 to 10, the dentifrice composition including a calcium ion source, a fluoride ion source and a phosphate ion source, wherein:
the calcium ion source and the phosphate ion source are unencapsulated and are provided by one or more calcium sucrose phosphate complexes, and
the fluoride ion source is encapsulated or coated in a coating impermeable to the toothpaste carrier and is provided by one or more amine fluorides,
whereby the coating degrades to release the fluoride ion source when mechanically agitated by a toothbrush in an oral cavity surface, and
wherein when the dentifrice composition is used with the toothbrush in an oral cavity, a tooth surface in the oral cavity is first exposed to the calcium ion source and the phosphate ion source before the coating degrades and the encapsulated fluoride ion source is released and the tooth surface is then exposed to the fluoride ion source.

2. A dentifrice composition according to claim 1 wherein said fluoride ion source is:
present in an available concentration of between 0.001 ppm to less than 1 ppm, or between 0.001 ppm to 9000 ppm, or 0.0025 to 0.09 ppm.

3. A dentifrice composition according to claim 1 wherein the impermeable coating material is selected from one or a combination of two or more of the group consisting of: hydroxyl propyl methyl cellulose (HPMC); HPMC acetate succinate; polyvinyl acetate phthalate (PVAP); shellac; waxes; fatty acids; fluoropolymers; polyvinyl alcohol-polyethylene glycol (PVA-PEG); polyvinyl-pyrrolidine (PVP); polyurethane; acrylic; alkyd; polyester; and methyl or ethyl cellulose.

4. A dentifrice composition according to claim 1 wherein said calcium ion source is present in an available concentration of between 500 ppm and 50,000 ppm.

5. A dentifrice composition according to claim 1, wherein the phosphate ion source is available at a concentration of between 500 ppm to 50,000 ppm.

6. A dentifrice composition according to claim 1, further comprising one or more acids or acidic buffers encapsulated in a coating impermeable to the toothpaste carrier, whereby the coating on the acids or buffers degrades to release the acid/s or buffer/s when mechanically agitated by a toothbrush thereby reducing the pH to a predetermined level.

7. A dentifrice composition according to claim 6, wherein release of acids or buffers results in a pH in the oral cavity of between 2.5 and 7.

8. A dentifrice composition according to claim 1, wherein the toothpaste carrier includes one or more alkaline materials or buffers encapsulated in a coating impermeable to a toothpaste carrier whereby the alkaline or buffer coating degrades to release the alkaline or buffer when in an acidic environment or in response to mechanical agitation by a toothbrush and thereby increase the pH in the oral cavity to a predetermined level.

9. A dentifrice composition according to claim 8 wherein the final pH in the oral cavity is between 6.0 and 8.0, or between 6.5 and 7.5, or is 7.5.

10. A dentifrice composition according to claim 1 wherein the carrier material further includes one or more antimicrobial materials selected from the group consisting of: chlorhexidine, chlorhexidine digluconate, benzalkonium chloride (BAC), Cetylpyridinium chloride (CPC), Kappazinc, Kappacin, and stabilised chlorine dioxide.

11. A method of cleaning teeth, the method comprising the steps of: providing an unencapsulated toothpaste carrier having a pH of 7 to 10;
disposing a calcium ion source in the toothpaste carrier such that the availability of the calcium ions is in the order of 500 ppm to 50,000 ppm;
disposing a phosphate ion source in the toothpaste carrier such that the availability of the phosphate ions is in the order of 500 ppm to 50,000 ppm;
disposing a fluoride ion source in the toothpaste carrier wherein the fluoride ion source is encapsulated or coated in an impermeable coating material such that the coating material is adapted to resist degradation in the presence of the toothpaste carrier and to degrade to expose the fluoride ion source upon application of the toothpaste carrier by a toothbrush to an oral cavity; wherein said fluoride ion source is present to provide an available fluoride ion concentration of between 0.0025 ppm to 9000 ppm; and
applying the toothpaste carrier to a tooth surface with a toothbrush, wherein the unencapsulated calcium ion source and phosphate ion source contact a tooth surface within the oral cavity before the coating material of the encapsulated fluoride ion source degrades to expose the tooth surface to the fluoride ion source, and wherein the calcium ion source and the phosphate ion source are provided by one or more calcium sucrose phosphate complexes and wherein the fluoride ion source is provided by one or more amine fluorides.

12. A method according to claim 11 including the step of coating said fluoride ion source in an impermeable coating material selected from one or a combination of two or more of the group consisting of: hydroxyl propyl methyl cellulose (HPMC); HPMC acetate succinate; polyvinyl acetate phthalate (PVAP); shellac; waxes; fatty acids; fluoropolymers; polyvinyl alcohol-polyethylene glycol (PVA-PEG); polyvinyl-pyrrolidine (PVP); polyurethane; acrylic; alkyd; polyester; and methyl or ethyl cellulose.

13. A method of assisting in tooth remineralization, the method comprising the steps of applying a toothpaste carrier material having a calcium ion source therein to a tooth surface wherein the toothpaste carrier includes a fluoride ion source encapsulated in an impermeable coating adapted to degrade upon application of the toothpaste carrier to the tooth surface to release said fluoride ion source after the toothpaste carrier has commenced application by a toothbrush in an oral cavity and after the calcium ion source has been applied to the tooth surface, wherein the calcium ion source is one or more calcium sucrose phosphate complexes and wherein the fluoride ion source is provided by one or more amine fluorides.

14. A method according to claim 11 wherein the pH in the oral cavity is modified by the inclusion of one or more acids or acidic buffers, wherein the acids or acidic buffers are encapsulated in a coating impermeable to the toothpaste carrier, and whereby the coating on the acids or acidic buffers releases the acids or acidic buffers when mechanically agitated by a toothbrush thereby reducing the pH in the oral cavity to a predetermined level.

15. A method according to claim 14, wherein release of the acids or buffers results in a pH in the oral cavity of between 2.5 and 7.

16. A method according to claim 13 wherein the pH of the toothpaste carrier includes one or more alkaline materials or buffers encapsulated in a coating impermeable to a toothpaste carrier whereby the alkaline or buffer coating degrades to release the alkaline or buffer when in an acidic environment or in response to mechanical agitation by a toothbrush and thereby increase the pH to a predetermined level.

17. A method according to claim 16 wherein the final pH in the oral cavity is between 6.0 and 8.0, or between 6.5 and 7.5, or is 7.5.

18. A method according to claim 13 wherein the toothpaste carrier is pH modified by the inclusion of one or more acids or acidic buffers encapsulated in a coating impermeable to the toothpaste carrier degrade whereby the coating on the one or more acids or buffers to release the one or more acids or buffers when mechanically agitated by a toothbrush thereby to reduce the pH to a predetermined level.

* * * * *